(12) United States Patent
Ichihara et al.

US010435684B2

(10) Patent No.: US 10,435,684 B2
(45) Date of Patent: Oct. 8, 2019

(54) SOPHOROLIPID HIGHLY-PRODUCTIVE MUTANT STRAIN

(71) Applicant: KAO CORPORATION, Chuo-ku, Tokyo (JP)

(72) Inventors: Takahiro Ichihara, Wakayama (JP); Masatoshi Tohata, Utsunomiya (JP); Atsuko Hayase, Haga (JP); Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 43 days.

(21) Appl. No.: 15/740,070

(22) PCT Filed: Jul. 15, 2016

(86) PCT No.: PCT/JP2016/070961
§ 371 (c)(1),
(2) Date: Dec. 27, 2017

(87) PCT Pub. No.: WO2017/014175
PCT Pub. Date: Jan. 26, 2017

(65) Prior Publication Data
US 2019/0062723 A1 Feb. 28, 2019

(30) Foreign Application Priority Data
Jul. 22, 2015 (JP) .................................. 2015-144760

(51) Int. Cl.
C12N 5/10 (2006.01)
C12P 19/44 (2006.01)
C12P 7/64 (2006.01)
C12N 15/10 (2006.01)

(52) U.S. Cl.
CPC .............. *C12N 15/102* (2013.01); *C12P 7/64* (2013.01); *C12P 19/44* (2013.01)

(58) Field of Classification Search
CPC ........... C12P 19/44; C12P 7/64; C12N 15/102
See application file for complete search history.

(56) References Cited

U.S. PATENT DOCUMENTS

| 8,530,206 B2 | 9/2013 | Develter et al. |
| 9,738,913 B2 * | 8/2017 | Beardslee ................ C12N 1/16 |
| 2012/0311741 A1 | 12/2012 | Soetaert et al. |
| 2015/0267235 A1 | 9/2015 | Takahashi |
| 2015/0353966 A1 | 12/2015 | Beardslee et al. |

FOREIGN PATENT DOCUMENTS

| EP | 2502932 A1 | 9/2012 |
| JP | 2003-009896 A | 1/2003 |
| JP | 2008-247845 A | 10/2008 |
| JP | 2014-150774 A | 8/2014 |
| JP | 2015-100290 A | 6/2015 |
| JP | 2015-104381 A | 6/2015 |
| WO | WO 2012/080116 A1 | 6/2012 |
| WO | WO 2014/061459 A1 | 4/2014 |
| WO | WO 2014/100461 A2 | 6/2014 |
| WO | WO 2014/100504 A2 | 6/2014 |

OTHER PUBLICATIONS

International Search Report (ISR) for PCT/JP2016/070961; I.A. fd Jul. 15, 2016, dated Oct. 18, 2016 from the Japan Patent Office, Tokyo, Japan.
International Preliminary Report on Patentability (IPRP), Chapter I of the Patent Cooperation Treaty, including the Written Opinion for PCT/JP2016/070961; I.A. fd Jul. 15, 2016, dated Jan. 23, 2018, by the International Bureau of WIPO, Geneva, Switzerland.
Van Bogaert, IN et al., "Microbial production and application of sophorolipids," Appl Microbiol Biotechnol. Aug. 2007;76(1):23-34. Epub May 3, 2007, Springer International, New York, NY.
Zerkowski, JA et al., "Head group-modified sophorolipids: Synthesis of new cationic, zwitterionic, and anionic surfactants," Journal of Surfactants and Detergents. Mar. 2006, vol. 9(1):57-62, AOCS Press, Champaign, IL.
Van Bogaert, IN et al., "Knocking out the MFE-2 gene of *Candida bombicola* leads to improved medium-chain sophorolipid production," FEMS Yeast Res. Jun. 2009;9(4):610-7. doi: 10.1111/j.1567-1364.2009.00501.x. Epub Mar. 17, 2009, Elsevier Science B.V., Amsterdam, Netherlands.
Von Roermund, CWT et al., "Fatty acid metabolism in *Saccharomyces cerevisiae*," Cell Mol Life Sci. Sep. 2003;60(9):1838-51, Birkhauser, Boston, MA.
Ciesielska, K. et al., "SILAC-based proteome analysis of *Starmerella bombicola* sophorolipid production," J Proteome Res. Oct. 4, 2013;12(10):4376-92. doi: 10.1021/pr400392a. Epub Sep. 11, 2013, American Chemical Society, Washington, DC.
Extended European search report including the supplementary European search report and the European search opinion, dated Dec. 13, 2018, for EP Appl. No. 16827735.8, European Patent Office, Munich , Germany.
Leber, C. et al., "Overproduction and secretion of free fatty acids through disrupted neutral lipid recycle in *Saccharomyces cerevisiae*," Metab Eng. Mar. 2015;28:54-62. doi: 10.1016/j.ymben.2014.11.006. Epub Nov. 25, 2014.

\* cited by examiner

*Primary Examiner* — Ganapathirama Raghu
(74) *Attorney, Agent, or Firm* — Sterne, Kessler, Goldstein & Fox P.L.L.C.

(57) ABSTRACT

Provided is a microorganism exhibiting high production capability for sophorolipids. Disclosed is a yeast mutant strain having high sophorolipid productivity, in which a transporter transporting Acyl-CoA to a peroxisome has been deleted or deactivated.

21 Claims, 1 Drawing Sheet
Specification includes a Sequence Listing.

[Figure 1]
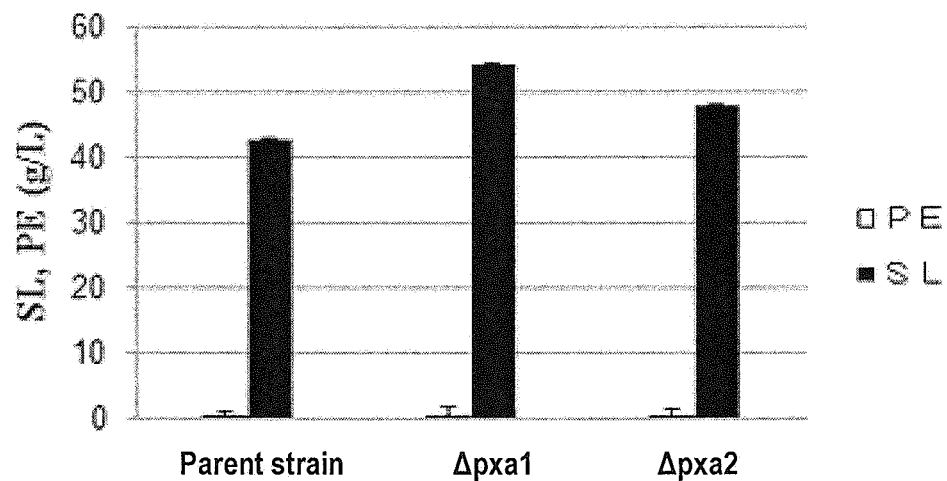
[Figure 2]
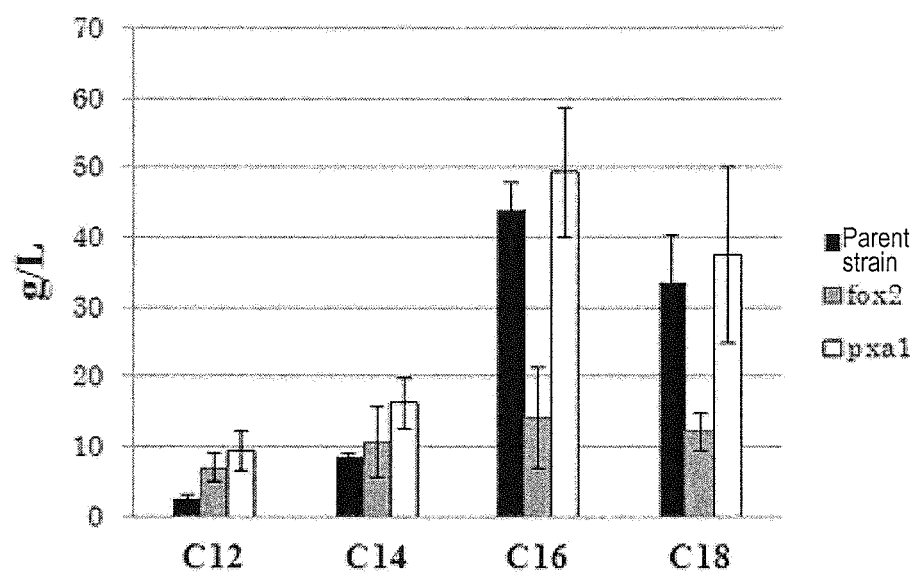

SEQUENCE LISTING

<160> NUMBER OF SEQ ID NOS: 23

<210> SEQ ID NO 1
<211> LENGTH: 2250
<212> TYPE: DNA
<213> ORGANISM: Starmerella bombicola
<220> FEATURE:
<221> NAME/KEY: CDS
<222> LOCATION: (1)..(2250)

<400> SEQUENCE: 1

```
gtg cat cgc atg gta cgg aac agg aat tct tta tct ata gaa gac ctg      48
Met His Arg Met Val Arg Asn Arg Asn Ser Leu Ser Ile Glu Asp Leu
  1               5                  10                  15 cga agc aag cct act gtg cta tgc ctt gct ttt cta gtc ata tac tat      96
Arg Ser Lys Pro Thr Val Leu Cys Leu Ala Phe Leu Val Ile Tyr Tyr
             20                  25                  30 tca aaa cgt tac agg gac agg aga aag ctg cgc gag tcc tca gag cgc     144
Ser Lys Arg Tyr Arg Asp Arg Arg Lys Leu Arg Glu Ser Ser Glu Arg
         35                  40                  45 gcc aat gct ctg ttg act tgt gac tct ccg gag aat gct act cat tta     192
Ala Asn Ala Leu Leu Thr Cys Asp Ser Pro Glu Asn Ala Thr His Leu
     50                  55                  60 cag gtt gcc tac aag aag ggc ttt gtg cac aag aga ata tgc cat tcc     240
Gln Val Ala Tyr Lys Lys Gly Phe Val His Lys Arg Ile Cys His Ser
 65                  70                  75                  80 tca caa gaa aag ttt gac cag gac ttc cgt aag ttc gcc aaa ttc aaa     288
Ser Gln Glu Lys Phe Asp Gln Asp Phe Arg Lys Phe Ala Lys Phe Lys
                 85                  90                  95 ggt agc ttt gga aag gag ctt tcc gca gtt ctg agt att atc atc cct     336
Gly Ser Phe Gly Lys Glu Leu Ser Ala Val Leu Ser Ile Ile Ile Pro
            100                 105                 110 aac tac aga tca aga gcc att cgg ctt ttg att ttg cat atg gct atg     384
Asn Tyr Arg Ser Arg Ala Ile Arg Leu Leu Ile Leu His Met Ala Met
        115                 120                 125 ctt gga ttg cga act tac atg tcc ctt ctg gtc gct gac ctt gat ggt     432
Leu Gly Leu Arg Thr Tyr Met Ser Leu Leu Val Ala Asp Leu Asp Gly
    130                 135                 140
```

```
cgt ata gtg cgg cac ctc atc gga gcc aac ggc cca gcc ttt gtt gcc      480
Arg Ile Val Arg His Leu Ile Gly Ala Asn Gly Pro Ala Phe Val Ala
145                 150                 155                 160 ggt ttg atg gag tgg cta ata ctt gct gtt cca gcg agc tac acc aat      528
Gly Leu Met Glu Trp Leu Ile Leu Ala Val Pro Ala Ser Tyr Thr Asn
                165                 170                 175 gca atg att aag tac ctc gag ggg aaa atc agc tta gaa ttc aga tca      576
Ala Met Ile Lys Tyr Leu Glu Gly Lys Ile Ser Leu Glu Phe Arg Ser
            180                 185                 190 aca atg gtg aga tac atc cac gat cta tat ctc ggt gcg aac aaa gaa      624
Thr Met Val Arg Tyr Ile His Asp Leu Tyr Leu Gly Ala Asn Lys Glu
        195                 200                 205 tac tac aag gtt tcc agc ata gat ggt gcg ctt caa gga att gac cat      672
Tyr Tyr Lys Val Ser Ser Ile Asp Gly Ala Leu Gln Gly Ile Asp His
    210                 215                 220 tat atc acg tcc gac gtg aca aag ttt tgt agc gct gcg gca aag ctg      720
Tyr Ile Thr Ser Asp Val Thr Lys Phe Cys Ser Ala Ala Ala Lys Leu
225                 230                 235                 240 tac tcc aat ttg ggc aag cca agt ctt gac ttg gta atc ttc gcg gtt      768
Tyr Ser Asn Leu Gly Lys Pro Ser Leu Asp Leu Val Ile Phe Ala Val
                245                 250                 255 cag ctg tca cgg aat ctt gga agg aaa act ctc gca ggg att ttc ctc      816
Gln Leu Ser Arg Asn Leu Gly Arg Lys Thr Leu Ala Gly Ile Phe Leu
            260                 265                 270 aac tat att gtt acc gct gct ctt ttg aga cag ttt tca cca gca ttc      864
Asn Tyr Ile Val Thr Ala Ala Leu Leu Arg Gln Phe Ser Pro Ala Phe
        275                 280                 285 ggt tct ttg gct gcc aag gag gcc cag ctg gaa ggc gaa tat cgc aac      912
Gly Ser Leu Ala Ala Lys Glu Ala Gln Leu Glu Gly Glu Tyr Arg Asn
    290                 295                 300 gct cac tct cgt gta atc acg aac gct gaa gag ata gct ttt tat gat      960
Ala His Ser Arg Val Ile Thr Asn Ala Glu Glu Ile Ala Phe Tyr Asp
305                 310                 315                 320 gga gcc tct atc gaa aag ctg agt tta ggc gaa tca tac cga tca ctt     1008
Gly Ala Ser Ile Glu Lys Leu Ser Leu Gly Glu Ser Tyr Arg Ser Leu
                325                 330                 335 gtc aag cat ata gcc cat gtc tcg aaa gtc aag gct tta tat tcg atc     1056
Val Lys His Ile Ala His Val Ser Lys Val Lys Ala Leu Tyr Ser Ile
            340                 345                 350 atg gag ggc tat gtt ctc aaa tat tcc tgg tca gcg tcc ggt tat tta     1104
Met Glu Gly Tyr Val Leu Lys Tyr Ser Trp Ser Ala Ser Gly Tyr Leu
        355                 360                 365 ttt gcc tcc gtc cct gtg ttt ttc ccg gct tct cga gga agc agc gtc     1152
Phe Ala Ser Val Pro Val Phe Phe Pro Ala Ser Arg Gly Ser Ser Val
    370                 375                 380 aat gtc att cca cca gcc aac agg gat gaa aga gaa aat atg gga aaa     1200
Asn Val Ile Pro Pro Ala Asn Arg Asp Glu Arg Glu Asn Met Gly Lys
385                 390                 395                 400 ttc gtg acg aac aaa cga atc atg ctc tcc atc tct gat gcc ggc ggt     1248
Phe Val Thr Asn Lys Arg Ile Met Leu Ser Ile Ser Asp Ala Gly Gly
                405                 410                 415 cga atc atg tac tcc atc aag gac atg gca gaa tta gca gga tac aca     1296
Arg Ile Met Tyr Ser Ile Lys Asp Met Ala Glu Leu Ala Gly Tyr Thr
            420                 425                 430 aga cgc gtc tac cag ctc ata gca gct ctg cac aga gta agg aac aat     1344
Arg Arg Val Tyr Gln Leu Ile Ala Ala Leu His Arg Val Arg Asn Asn
        435                 440                 445 gct tat cga cct cat agt gat aga agg gtc gag gaa aag caa gag aat     1392
Ala Tyr Arg Pro His Ser Asp Arg Arg Val Glu Glu Lys Gln Glu Asn
    450                 455                 460
```

-continued

```
aaa caa gag acc ggc gaa tct gac agt tac aca cta gcg gat gtc aaa     1440
Lys Gln Glu Thr Gly Glu Ser Asp Ser Tyr Thr Leu Ala Asp Val Lys
465                 470                 475                 480 ggt aag ctt gaa atc tca acg act tgt gag aca gtt tct ttc gaa aag     1488
Gly Lys Leu Glu Ile Ser Thr Thr Cys Glu Thr Val Ser Phe Glu Lys
            485                 490                 495 gtg cct gtc gta gta cct ggc tca ggc gtt gaa atg tct aag ggt gaa     1536
Val Pro Val Val Val Pro Gly Ser Gly Val Glu Met Ser Lys Gly Glu
        500                 505                 510 gcc ata ctg gat cca ctc act ttt gaa gtg act cct ggc cag cac ttg     1584
Ala Ile Leu Asp Pro Leu Thr Phe Glu Val Thr Pro Gly Gln His Leu
    515                 520                 525 ctt gtc ata gga tct aac ggc tct ggg aag tcc tca att gct cgc ctt     1632
Leu Val Ile Gly Ser Asn Gly Ser Gly Lys Ser Ser Ile Ala Arg Leu
530                 535                 540 gct gca gga ctc tgg cct atc tat aga ggg cta tta ctg aga tcc agt     1680
Ala Ala Gly Leu Trp Pro Ile Tyr Arg Gly Leu Leu Leu Arg Ser Ser
545                 550                 555                 560 aaa gta gcg ttt ctc ccg cag agg cct tac ttt agc acg ggg aca ttg     1728
Lys Val Ala Phe Leu Pro Gln Arg Pro Tyr Phe Ser Thr Gly Thr Leu
            565                 570                 575 cgc gac caa atc ata tac cca caa aca cgc gac tct cta atc cgt aac     1776
Arg Asp Gln Ile Ile Tyr Pro Gln Thr Arg Asp Ser Leu Ile Arg Asn
        580                 585                 590 agc ttc ctg gac agt gac ttg ctg cag att ttg cgt cga gtg cat ttg     1824
Ser Phe Leu Asp Ser Asp Leu Leu Gln Ile Leu Arg Arg Val His Leu
    595                 600                 605 gac tac tta cct gaa cgc gag gga gga ttt gac gtt aca aag gaa tgg     1872
Asp Tyr Leu Pro Glu Arg Glu Gly Gly Phe Asp Val Thr Lys Glu Trp
610                 615                 620 aaa gat gta ctg agt ggg ggc gag aag cag cgt atg ctt ttt gct agg     1920
Lys Asp Val Leu Ser Gly Gly Glu Lys Gln Arg Met Leu Phe Ala Arg
625                 630                 635                 640 ctt ttg ttt gcc aag cca agg ttc gca att atc gat gag gga aca tcg     1968
Leu Leu Phe Ala Lys Pro Arg Phe Ala Ile Ile Asp Glu Gly Thr Ser
            645                 650                 655 gca gtc agc gca gac atg gaa ggg ctt ttg tat gaa gag tgc aaa gcc     2016
Ala Val Ser Ala Asp Met Glu Gly Leu Leu Tyr Glu Glu Cys Lys Ala
        660                 665                 670 gac gga ata acg ctg atc aca att tca cac aga ctg tct ctt ctg aaa     2064
Asp Gly Ile Thr Leu Ile Thr Ile Ser His Arg Leu Ser Leu Leu Lys
    675                 680                 685 tac cat ggg act aag tta gag gtc ggt ctt gga gag gat gga gcg gag     2112
Tyr His Gly Thr Lys Leu Glu Val Gly Leu Gly Glu Asp Gly Ala Glu
690                 695                 700 tgg tcc tta gag aat act gct cac gaa cag ggt tgg agc agc atg gac     2160
Trp Ser Leu Glu Asn Thr Ala His Glu Gln Gly Trp Ser Ser Met Asp
705                 710                 715                 720 aaa gag ata gaa gac att cag aac ttt ctt tcc aca gtt ccc gca ttg     2208
Lys Glu Ile Glu Asp Ile Gln Asn Phe Leu Ser Thr Val Pro Ala Leu
            725                 730                 735 gag aaa agg agg cgg gaa gtt ttg gag cta ctt cgt gct taa             2250
Glu Lys Arg Arg Arg Glu Val Leu Glu Leu Leu Arg Ala
            740                 745
```

<210> SEQ ID NO 2
<211> LENGTH: 749
<212> TYPE: PRT
<213> ORGANISM: Starmerella bombicola

<400> SEQUENCE: 2

```
Met His Arg Met Val Arg Asn Arg Asn Ser Leu Ser Ile Glu Asp Leu
1               5                   10                  15

Arg Ser Lys Pro Thr Val Leu Cys Leu Ala Phe Leu Val Ile Tyr Tyr
            20                  25                  30

Ser Lys Arg Tyr Arg Asp Arg Arg Lys Leu Arg Glu Ser Glu Arg
        35                  40                  45

Ala Asn Ala Leu Leu Thr Cys Asp Ser Pro Glu Asn Ala Thr His Leu
    50                  55                  60

Gln Val Ala Tyr Lys Lys Gly Phe Val His Lys Arg Ile Cys His Ser
65              70                  75                  80

Ser Gln Glu Lys Phe Asp Gln Asp Phe Arg Lys Phe Ala Lys Phe Lys
                85                  90                  95

Gly Ser Phe Gly Lys Glu Leu Ser Ala Val Leu Ser Ile Ile Ile Pro
            100                 105                 110

Asn Tyr Arg Ser Arg Ala Ile Arg Leu Leu Ile Leu His Met Ala Met
        115                 120                 125

Leu Gly Leu Arg Thr Tyr Met Ser Leu Leu Val Ala Asp Leu Asp Gly
    130                 135                 140

Arg Ile Val Arg His Leu Ile Gly Ala Asn Gly Pro Ala Phe Val Ala
145                 150                 155                 160

Gly Leu Met Glu Trp Leu Ile Leu Ala Val Pro Ala Ser Tyr Thr Asn
                165                 170                 175

Ala Met Ile Lys Tyr Leu Glu Gly Lys Ile Ser Leu Glu Phe Arg Ser
            180                 185                 190

Thr Met Val Arg Tyr Ile His Asp Leu Tyr Leu Gly Ala Asn Lys Glu
        195                 200                 205

Tyr Tyr Lys Val Ser Ser Ile Asp Gly Ala Leu Gln Gly Ile Asp His
    210                 215                 220

Tyr Ile Thr Ser Asp Val Thr Lys Phe Cys Ser Ala Ala Ala Lys Leu
225                 230                 235                 240

Tyr Ser Asn Leu Gly Lys Pro Ser Leu Asp Leu Val Ile Phe Ala Val
                245                 250                 255

Gln Leu Ser Arg Asn Leu Gly Arg Lys Thr Leu Ala Gly Ile Phe Leu
            260                 265                 270

Asn Tyr Ile Val Thr Ala Ala Leu Leu Arg Gln Phe Ser Pro Ala Phe
        275                 280                 285

Gly Ser Leu Ala Ala Lys Glu Ala Gln Leu Glu Gly Glu Tyr Arg Asn
    290                 295                 300

Ala His Ser Arg Val Ile Thr Asn Ala Glu Glu Ile Ala Phe Tyr Asp
305                 310                 315                 320

Gly Ala Ser Ile Glu Lys Leu Ser Leu Gly Glu Ser Tyr Arg Ser Leu
                325                 330                 335

Val Lys His Ile Ala His Val Ser Lys Val Lys Ala Leu Tyr Ser Ile
            340                 345                 350

Met Glu Gly Tyr Val Leu Lys Tyr Ser Trp Ser Ala Ser Gly Tyr Leu
        355                 360                 365

Phe Ala Ser Val Pro Val Phe Phe Pro Ala Ser Arg Gly Ser Ser Val
    370                 375                 380

Asn Val Ile Pro Pro Ala Asn Arg Asp Glu Arg Glu Asn Met Gly Lys
385                 390                 395                 400

Phe Val Thr Asn Lys Arg Ile Met Leu Ser Ile Ser Asp Ala Gly Gly
                405                 410                 415
```

```
Arg Ile Met Tyr Ser Ile Lys Asp Met Ala Glu Leu Ala Gly Tyr Thr
            420                 425                 430

Arg Arg Val Tyr Gln Leu Ile Ala Ala Leu His Arg Val Arg Asn Asn
            435                 440                 445

Ala Tyr Arg Pro His Ser Asp Arg Arg Val Glu Lys Gln Glu Asn
450                 455                 460

Lys Gln Glu Thr Gly Glu Ser Asp Ser Tyr Thr Leu Ala Asp Val Lys
465                 470                 475                 480

Gly Lys Leu Glu Ile Ser Thr Thr Cys Glu Thr Val Ser Phe Glu Lys
            485                 490                 495

Val Pro Val Val Pro Gly Ser Gly Val Glu Met Ser Lys Gly Glu
            500                 505                 510

Ala Ile Leu Asp Pro Leu Thr Phe Glu Val Thr Pro Gly Gln His Leu
            515                 520                 525

Leu Val Ile Gly Ser Asn Gly Ser Gly Lys Ser Ser Ile Ala Arg Leu
            530                 535                 540

Ala Ala Gly Leu Trp Pro Ile Tyr Arg Gly Leu Leu Arg Ser Ser
545                 550                 555                 560

Lys Val Ala Phe Leu Pro Gln Arg Pro Tyr Phe Ser Thr Gly Thr Leu
            565                 570                 575

Arg Asp Gln Ile Ile Tyr Pro Gln Thr Arg Asp Ser Leu Ile Arg Asn
            580                 585                 590

Ser Phe Leu Asp Ser Asp Leu Leu Gln Ile Leu Arg Arg Val His Leu
            595                 600                 605

Asp Tyr Leu Pro Glu Arg Glu Gly Gly Phe Asp Val Thr Lys Glu Trp
            610                 615                 620

Lys Asp Val Leu Ser Gly Gly Glu Lys Gln Arg Met Leu Phe Ala Arg
625                 630                 635                 640

Leu Leu Phe Ala Lys Pro Arg Phe Ala Ile Ile Asp Glu Gly Thr Ser
            645                 650                 655

Ala Val Ser Ala Asp Met Glu Gly Leu Leu Tyr Glu Glu Cys Lys Ala
            660                 665                 670

Asp Gly Ile Thr Leu Ile Thr Ile Ser His Arg Leu Ser Leu Leu Lys
            675                 680                 685

Tyr His Gly Thr Lys Leu Glu Val Gly Leu Gly Glu Asp Gly Ala Glu
            690                 695                 700

Trp Ser Leu Glu Asn Thr Ala His Gly Gln Gly Trp Ser Ser Met Asp
705                 710                 715                 720

Lys Glu Ile Glu Asp Ile Gln Asn Phe Leu Ser Thr Val Pro Ala Leu
            725                 730                 735

Glu Lys Arg Arg Arg Glu Val Leu Glu Leu Leu Arg Ala
            740                 745

<210> SEQ ID NO 3
<211> LENGTH: 2097
<212> TYPE: DNA
<213> ORGANISM: Starmerella bombicola
<220> FEATURE:
<221> NAME/KEY: CDS
<222> LOCATION: (1)..(2097)

<400> SEQUENCE: 3 atg att agg ctg agc tcg ttt tct act agt tcg gtc ggt cat gcg tac      48
Met Ile Arg Leu Ser Ser Phe Ser Thr Ser Ser Val Gly His Ala Tyr
 1               5                   10                  15
```

-continued

| | | |
|---|---|---|
| cat tcc cat cgc cga ggc ata acc aga gct ctt tac aca acg ttg cta<br>His Ser His Arg Arg Gly Ile Thr Arg Ala Leu Tyr Thr Thr Leu Leu<br>                    20                    25                    30 | 96 |
| gca tcc ttc ggg att cgg gtt tac cgt act att att tcc gag aag aaa<br>Ala Ser Phe Gly Ile Arg Val Tyr Arg Thr Ile Ile Ser Glu Lys Lys<br>                    35                    40                    45 | 144 |
| aat aag agt gga aag cca aga gtt gct gtc aac gct act ttc ctc cgg<br>Asn Lys Ser Gly Lys Pro Arg Val Ala Val Asn Ala Thr Phe Leu Arg<br> 50                        55                    60 | 192 |
| aac ctg ctt aga ctg ctt cgc gtg gca atc cct tcg cct ttc tcg aat<br>Asn Leu Leu Arg Leu Leu Arg Val Ala Ile Pro Ser Pro Phe Ser Asn<br> 65                    70                    75                  80 | 240 |
| gac aca ctg ctt gtt ctg ctg caa gca gtt gct ctc atc att cga acg<br>Asp Thr Leu Leu Val Leu Leu Gln Ala Val Ala Leu Ile Ile Arg Thr<br>                    85                    90                    95 | 288 |
| tac cta agt ctt tcc ata gcc cgc ctc gat ggg cta atc act gct ctg<br>Tyr Leu Ser Leu Ser Ile Ala Arg Leu Asp Gly Leu Ile Thr Ala Leu<br>                  100                  105                 110 | 336 |
| cta att cgt ggt gag ggg aaa aag ttc gtg cgt gca gta gct ctt tgg<br>Leu Ile Arg Gly Glu Gly Lys Lys Phe Val Arg Ala Val Ala Leu Trp<br>                  115                  120                 125 | 384 |
| atg gcg att ggt gtg cca gca gca gct gta aat gca gcc att caa ttt<br>Met Ala Ile Gly Val Pro Ala Ala Ala Val Asn Ala Ala Ile Gln Phe<br>130                    135                  140 | 432 |
| ctt atg cga cgt att gcg tta cgc atc cgc aca cga ctc aca gat tat<br>Leu Met Arg Arg Ile Ala Leu Arg Ile Arg Thr Arg Leu Thr Asp Tyr<br>145                    150                  155                 160 | 480 |
| gcc ctc gac cgg tac ctc gtt cag ggt cac cag cag ccg gtt tac tat<br>Ala Leu Asp Arg Tyr Leu Val Gln Gly His Gln Gln Pro Val Tyr Tyr<br>                  165                  170                 175 | 528 |
| ggt att cag cag cat gag agc gtg aat gtt ggt caa ctt atg gcc gca<br>Gly Ile Gln Gln His Glu Ser Val Asn Val Gly Gln Leu Met Ala Ala<br>                  180                  185                 190 | 576 |
| gat att gca aaa ttc tct gct tct ctt tcg aag ctc tac tca aat ctt<br>Asp Ile Ala Lys Phe Ser Ala Ser Leu Ser Lys Leu Tyr Ser Asn Leu<br>                  195                  200                 205 | 624 |
| gcg aag cca att ttg gat gtc tcg gtc tac acg tac caa ttg agc aag<br>Ala Lys Pro Ile Leu Asp Val Ser Val Tyr Thr Tyr Gln Leu Ser Lys<br>210                    215                  220 | 672 |
| agt atc ggc gga gac aat gta ttc ttg ctg ggc ctg acg att cag ctc<br>Ser Ile Gly Gly Asp Asn Val Phe Leu Leu Gly Leu Thr Ile Gln Leu<br>225                    230                  235                 240 | 720 |
| agc gct cag gca ctg agg cta gcc gct ccg ccg ttt gga gag ttc gtg<br>Ser Ala Gln Ala Leu Arg Leu Ala Ala Pro Pro Phe Gly Glu Phe Val<br>                  245                  250                 255 | 768 |
| gcc tct gaa gca aag cta gag ggc gac ttc cgc gcc gcg cac tca cgg<br>Ala Ser Glu Ala Lys Leu Glu Gly Asp Phe Arg Ala Ala His Ser Arg<br>                  260                  265                 270 | 816 |
| ctt gtg gag tat gcc gag gag gtt gcg ttc tac gac ggc aat atc ccc<br>Leu Val Glu Tyr Ala Glu Glu Val Ala Phe Tyr Asp Gly Asn Ile Pro<br>                  275                  280                 285 | 864 |
| gaa aga caa aga ctg gac acg cga ttt tat gcc ctt gct aag cat gtt<br>Glu Arg Gln Arg Leu Asp Thr Arg Phe Tyr Ala Leu Ala Lys His Val<br>                290                    295                 300 | 912 |
| gat cgt gtc tta agg cac cgg ctt gcg tac gct tcg ctc gaa gat ttc<br>Asp Arg Val Leu Arg His Arg Leu Ala Tyr Ala Ser Leu Glu Asp Phe<br>305                    310                  315                 320 | 960 |
| gtt gtg aag tac tgg tgg ggt gcc gca gga ctt gtg ctg tgc tcc att<br>Val Val Lys Tyr Trp Trp Gly Ala Ala Gly Leu Val Leu Cys Ser Ile<br>                  325                  330                 335 | 1008 |

```
ccc gtt ttt agt ggc agc agc gac tct cgt caa cgc gca cag act ttc    1056
Pro Val Phe Ser Gly Ser Ser Asp Ser Arg Gln Arg Ala Gln Thr Phe
        340                 345                 350 gtg gtc aac cgt aaa ctt ctt ctc ttg agc agc gat gct gtc gga cgt    1104
Val Val Asn Arg Lys Leu Leu Leu Leu Ser Ser Asp Ala Val Gly Arg
            355                 360                 365 atc atg tcg agt tac aaa gag atc agc tcg ttg gca ggt atg acc gca    1152
Ile Met Ser Ser Tyr Lys Glu Ile Ser Ser Leu Ala Gly Met Thr Ala
370                 375                 380 cgt gtg acc gag ttt ttc gac gaa atc acg tct ctg gct gtg gca act    1200
Arg Val Thr Glu Phe Phe Asp Glu Ile Thr Ser Leu Ala Val Ala Thr
385                 390                 395                 400 ccg ttc cca agt cgc ata gag gca gtg gaa ggt gag ggc act caa aac    1248
Pro Phe Pro Ser Arg Ile Glu Ala Val Glu Gly Glu Gly Thr Gln Asn
            405                 410                 415 cgc ata atc gaa att ggg gat att gaa ggc gaa aag agt gcg cca agt    1296
Arg Ile Ile Glu Ile Gly Asp Ile Glu Gly Glu Lys Ser Ala Pro Ser
            420                 425                 430 caa ctt gac cct gga cga gtc ata gtt ggt gat cga att gag ttc gat    1344
Gln Leu Asp Pro Gly Arg Val Ile Val Gly Asp Arg Ile Glu Phe Asp
        435                 440                 445 caa gtg cct atc gtg agc cct act ggt gag acg ctt gtc aaa gac ctc    1392
Gln Val Pro Ile Val Ser Pro Thr Gly Glu Thr Leu Val Lys Asp Leu
450                 455                 460 tcg ttt cgc ata gat caa ggc cat cac ctg ctc att gtc ggc cct aat    1440
Ser Phe Arg Ile Asp Gln Gly His His Leu Leu Ile Val Gly Pro Asn
465                 470                 475                 480 ggt agc ggt aag tcc tcc ttg ttc cgt atc cta gga ggc ctt tgg cca    1488
Gly Ser Gly Lys Ser Ser Leu Phe Arg Ile Leu Gly Gly Leu Trp Pro
            485                 490                 495 gta act gca ggc cgc gta ata cgc ccc aaa cat aac gag atg ttt tac    1536
Val Thr Ala Gly Arg Val Ile Arg Pro Lys His Asn Glu Met Phe Tyr
            500                 505                 510 att cct cag cga cca tac ctc agc cat ggc tcg ttg cgg caa caa att    1584
Ile Pro Gln Arg Pro Tyr Leu Ser His Gly Ser Leu Arg Gln Gln Ile
        515                 520                 525 att tat cca atc tcc gaa aag gag aac act gta agt gac gct gaa ctg    1632
Ile Tyr Pro Ile Ser Glu Lys Glu Asn Thr Val Ser Asp Ala Glu Leu
        530                 535                 540 aat gag att tta gag gta ctt ggc ctc cag cat cta gta gag tcc gtc    1680
Asn Glu Ile Leu Glu Val Leu Gly Leu Gln His Leu Val Glu Ser Val
545                 550                 555                 560 ggc gga tgg gac gcc gtg aga gag tgg cgc gag gat ctg agc atg gga    1728
Gly Gly Trp Asp Ala Val Arg Glu Trp Arg Glu Asp Leu Ser Met Gly
            565                 570                 575 gct caa caa aag atc gcc gcg gcc agg ctt ttt tac cac aga cct aag    1776
Ala Gln Gln Lys Ile Ala Ala Ala Arg Leu Phe Tyr His Arg Pro Lys
            580                 585                 590 ttt gcg att cta gac gag tgc acg gca tca gtg aca ctc gac acc gaa    1824
Phe Ala Ile Leu Asp Glu Cys Thr Ala Ser Val Thr Leu Asp Thr Glu
        595                 600                 605 act acc ata tac aca cac gcc cag gag ctt ggt att tct ctg ctc aca    1872
Thr Thr Ile Tyr Thr His Ala Gln Glu Leu Gly Ile Ser Leu Leu Thr
        610                 615                 620 gtc tcc cac cgc gcc tct ctc tgg caa tat cat gac aaa ata tta cag    1920
Val Ser His Arg Ala Ser Leu Trp Gln Tyr His Asp Lys Ile Leu Gln
625                 630                 635                 640 ttt gac ggg caa gga cat tac ata ttt gca gat ctc aat cct tcg gaa    1968
Phe Asp Gly Gln Gly His Tyr Ile Phe Ala Asp Leu Asn Pro Ser Glu
```

```
                             645                 650                 655
cgg ttg gct ctc gaa gaa gaa aag ttg aaa atc gat tat cag ttg agg      2016
Arg Leu Ala Leu Glu Glu Glu Lys Leu Lys Ile Asp Tyr Gln Leu Arg
            660                 665                 670 cag gtc gag cag ctg aaa gag cgt ctc tca gct ctc gag caa cag aag      2064
Gln Val Glu Gln Leu Lys Glu Arg Leu Ser Ala Leu Glu Gln Gln Lys
        675                 680                 685 cta cgc agg ccg tca gac act tcc gtt tgt tag                          2097
Leu Arg Arg Pro Ser Asp Thr Ser Val Cys
        690                 695

<210> SEQ ID NO 4
<211> LENGTH: 698
<212> TYPE: PRT
<213> ORGANISM: Starmerella bombicola

<400> SEQUENCE: 4

Met Ile Arg Leu Ser Ser Phe Ser Thr Ser Ser Val Gly His Ala Tyr
1               5                   10                  15

His Ser His Arg Arg Gly Ile Thr Arg Ala Leu Tyr Thr Thr Leu Leu
            20                  25                  30

Ala Ser Phe Gly Ile Arg Val Tyr Arg Thr Ile Ile Ser Glu Lys Lys
        35                  40                  45

Asn Lys Ser Gly Lys Pro Arg Val Ala Val Asn Ala Thr Phe Leu Arg
    50                  55                  60

Asn Leu Leu Arg Leu Arg Val Ala Ile Pro Ser Pro Phe Ser Asn
65                  70                  75                  80

Asp Thr Leu Leu Val Leu Leu Gln Ala Val Ala Leu Ile Ile Arg Thr
                85                  90                  95

Tyr Leu Ser Leu Ser Ile Ala Arg Leu Asp Gly Leu Ile Thr Ala Leu
            100                 105                 110

Leu Ile Arg Gly Glu Gly Lys Lys Phe Val Arg Ala Val Ala Leu Trp
        115                 120                 125

Met Ala Ile Gly Val Pro Ala Ala Val Asn Ala Ala Ile Gln Phe
    130                 135                 140

Leu Met Arg Arg Ile Ala Leu Arg Ile Arg Thr Arg Leu Thr Asp Tyr
145                 150                 155                 160

Ala Leu Asp Arg Tyr Leu Val Gln Gly His Gln Gln Pro Val Tyr Tyr
                165                 170                 175

Gly Ile Gln Gln His Glu Ser Val Asn Val Gly Gln Leu Met Ala Ala
            180                 185                 190

Asp Ile Ala Lys Phe Ser Ala Ser Leu Ser Lys Leu Tyr Ser Asn Leu
        195                 200                 205

Ala Lys Pro Ile Leu Asp Val Ser Val Tyr Thr Tyr Gln Leu Ser Lys
    210                 215                 220

Ser Ile Gly Gly Asp Asn Val Phe Leu Leu Gly Leu Thr Ile Gln Leu
225                 230                 235                 240

Ser Ala Gln Ala Leu Arg Leu Ala Ala Pro Pro Phe Gly Glu Phe Val
                245                 250                 255

Ala Ser Glu Ala Lys Leu Glu Gly Asp Phe Arg Ala Ala His Ser Arg
            260                 265                 270

Leu Val Glu Tyr Ala Glu Val Ala Phe Tyr Asp Gly Asn Ile Pro
        275                 280                 285

Glu Arg Gln Arg Leu Asp Thr Arg Phe Tyr Ala Leu Ala Lys His Val
    290                 295                 300
```

Asp Arg Val Leu Arg His Arg Leu Ala Tyr Ala Ser Leu Glu Asp Phe
305                 310                 315                 320

Val Val Lys Tyr Trp Trp Gly Ala Ala Gly Leu Val Leu Cys Ser Ile
            325                 330                 335

Pro Val Phe Ser Gly Ser Asp Ser Arg Gln Arg Ala Gln Thr Phe
        340                 345                 350

Val Val Asn Arg Lys Leu Leu Leu Ser Ser Asp Ala Val Gly Arg
    355                 360                 365

Ile Met Ser Ser Tyr Lys Glu Ile Ser Ser Leu Ala Gly Met Thr Ala
370                 375                 380

Arg Val Thr Glu Phe Phe Asp Glu Ile Thr Ser Leu Ala Val Ala Thr
385                 390                 395                 400

Pro Phe Pro Ser Arg Ile Glu Ala Val Glu Gly Gly Thr Gln Asn
        405                 410                 415

Arg Ile Ile Glu Ile Gly Asp Ile Glu Gly Glu Lys Ser Ala Pro Ser
            420                 425                 430

Gln Leu Asp Pro Gly Arg Val Ile Val Gly Asp Arg Ile Glu Phe Asp
            435                 440                 445

Gln Val Pro Ile Val Ser Pro Thr Gly Glu Thr Leu Val Lys Asp Leu
450                 455                 460

Ser Phe Arg Ile Asp Gln Gly His His Leu Leu Ile Val Gly Pro Asn
465                 470                 475                 480

Gly Ser Gly Lys Ser Ser Leu Phe Arg Ile Leu Gly Gly Leu Trp Pro
                485                 490                 495

Val Thr Ala Gly Arg Val Ile Arg Pro Lys His Asn Glu Met Phe Tyr
            500                 505                 510

Ile Pro Gln Arg Pro Tyr Leu Ser His Gly Ser Leu Arg Gln Gln Ile
        515                 520                 525

Ile Tyr Pro Ile Ser Glu Lys Glu Asn Thr Val Ser Asp Ala Glu Leu
    530                 535                 540

Asn Glu Ile Leu Glu Val Leu Gly Leu Gln His Leu Val Glu Ser Val
545                 550                 555                 560

Gly Gly Trp Asp Ala Val Arg Glu Trp Arg Glu Asp Leu Ser Met Gly
            565                 570                 575

Ala Gln Gln Lys Ile Ala Ala Arg Leu Phe Tyr His Arg Pro Lys
        580                 585                 590

Phe Ala Ile Leu Asp Glu Cys Thr Ala Ser Val Thr Leu Asp Thr Glu
            595                 600                 605

Thr Thr Ile Tyr Thr His Ala Gln Glu Leu Gly Ile Ser Leu Leu Thr
    610                 615                 620

Val Ser His Arg Ala Ser Leu Trp Gln Tyr His Asp Lys Ile Leu Gln
625                 630                 635                 640

Phe Asp Gly Gln Gly His Tyr Ile Phe Ala Asp Leu Asn Pro Ser Glu
            645                 650                 655

Arg Leu Ala Leu Glu Glu Glu Lys Leu Lys Ile Asp Tyr Gln Leu Arg
            660                 665                 670

Gln Val Glu Gln Leu Lys Glu Arg Leu Ser Ala Leu Glu Gln Gln Lys
    675                 680                 685

Leu Arg Arg Pro Ser Asp Thr Ser Val Cys
        690                 695

<210> SEQ ID NO 5
<211> LENGTH: 1026
<212> TYPE: DNA

<213> ORGANISM: Escherichia coli

<400> SEQUENCE: 5

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatacgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg gcccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag gtcgatgcg acgcaatcgt ccgatccgga     900
gccgggactg tcgggcgtac acaaatcgcc cgcagaagcg cggccgtctg gaccgatggc     960
tgtgtagaag tacttgccga tagtggaaac cgacgcccca gcactcgtcc gagggcaaag    1020
gaatag                                                              1026
```

<210> SEQ ID NO 6
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 6

```
attttggaga gtttgtgact gctttatcaa                                      30
```

<210> SEQ ID NO 7
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 7

```
gttgcgagct gtttcgaaaa ttacactatc atccggagcg tgtgggtca                 50
```

<210> SEQ ID NO 8
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 8

```
ggcatcaatt aatcacaact agctttctcg                                      30
```

<210> SEQ ID NO 9
<211> LENGTH: 50

<212> TYPE: DNA
<213> ORGANISM: Artificial sequence
<220> FEATURE:
<223> OTHER INFORMATION: Synthetic oligonucleotide

<400> SEQUENCE: 9
gttgcgagct gtttcgaaaa ttgaactaaa gttctccgtg cagatatttg        50

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 10
ctgaattctc ctaagcattt aactgccttg        30

<210> SEQ ID NO 11
<211> LENGTH: 50
<212> TYPE: DNA
<213> ORGANISM: Artificial sequence
<220> FEATURE:
<223> OTHER INFORMATION: synthetic oligonucleotide

<400> SEQUENCE: 11
gttgcgagct gtttcgaaaa gtttcacttt cccttcttgt attttcaatg        50

<210> SEQ ID NO 12
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 12
tgtatagtga cgatgatgaa tttggctaca actaccatca gggtcgttag        50

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 13
tgagatgaca cacgtgacat gtcgatccta        30

<210> SEQ ID NO 14
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 14
tgtatagtga cgatgatgaa cgatcttgcg aacgctaaaa ccagtagttt        50

<210> SEQ ID NO 15
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 15
tagcgcagag cagtatgccc ccttcttccc                                    30

<210> SEQ ID NO 16
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 16
tgtatagtga cgatgatgaa cggagaagct atatagttaa ataaataaga              50

<210> SEQ ID NO 17
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 17
atgcataatg tgcgcttccg ctctgagaca                                    30

<210> SEQ ID NO 18
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 18
cactactgta gagaaataat atgaaaaagc ctgaactcac                         40

<210> SEQ ID NO 19
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 19
gaaggaactg tttgagaaaa ttatgaacaa acgacccaac                         40

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
ttttcgaaac agctcgcaac gatc                                          24

<210> SEQ ID NO 21
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 21
gtgagttcag gcttttcat attatttctc tacagtagtg                          40

<210> SEQ ID NO 22
<211> LENGTH: 40
<212> TYPE: DNA
<213> ORGANISM: Artificial sequence

```
<220> FEATURE:
<223> OTHER INFORMATION: Synthetic oligonucleotide

<400> SEQUENCE: 22
gttgggtcgt tgttcataa ttttctcaaa cagttccttc                            40

<210> SEQ ID NO 23
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 23
ttcatcatcg tcactataca catc                                            24
```

SOPHOROLIPID HIGHLY-PRODUCTIVE MUTANT STRAIN

REFERENCE TO SEQUENCE LISTING SUBMITTED ELECTRONICALLY

The content of the electronically submitted substitute sequence listing, file name 2537-1420001-Sequence-Listing.txt, size 35,798 bytes; and date of creation Apr. 13, 2018, filed herewith, is incorporated herein by reference in its entirety.

FIELD OF THE INVENTION

The present invention relates to a mutant strain having high sophorolipid productivity, and a method for producing a sophorolipid using the mutant strain.

BACKGROUND OF THE INVENTION

Sophorolipids are glycolipids which are produced by microorganisms, primarily by yeast species and in which long-chain hydroxy fatty acids are bonded to sophorose. Since sophorolipids are amphiphilic lipids having strong surface activityandexcellentbiodegradability,attentionhas- beenpaid in recent years to the use of sophorolipids as biosurfactants. Sincesophorolipidsareproductsofmicroorganisms,andnonionic components are main constituents thereof, sophorolipids are highly dermatotropic. Therefore, sophorolipids are used as penetration enhancers for cosmetic products. Furthermore, since sophorolipids have excellent biodegradability and are highly effective even when added in small amounts, the use of sophorolipids is also increasing in the field of cleaning agents such as detergents for dishwashing.

Regarding the yeast species that produces sophorolipids, *Starmerella bombicola* [old name: *Candida bombicola*], which is a non-pathogenic, basidiomycetous yeast, is well known. The sophorolipids produced by *Starmerella bombicola* have a lactone type or acid type structure, have a critical micelle concentration of 40 to 100 mg/L, and decrease the surface tension of water from 72.8 mN/m to 30 mN/m (Non Patent Literature 1). Sophorolipids show different physicochemical properties depending on the difference in structure. It has been reported that properties such as antibacterial properties and surface activity vary between the lactone type and the acid type of sophorolipids, or between different fatty acid species that constitute the sophorolipids (Non Patent Literatures 1 and 2).

In a case where sophorolipids are used as cleaning agents or cosmetic materials, competition with the surfactants that are currently used cannot be avoided. Conventionally, since general surfactants are bulk chemical agents, those general surfactants have been produced at very low cost. Therefore, reduction of the production cost of sophorolipids is strongly desired. Furthermore, in order to extend the scope of the usability of sophorolipids, production of sophorolipids having constituent fatty acids with various chain lengths is desirable.

In regard to the production process for sophorolipids, studies and improvements have been hitherto made mainly on, for example, the yield, purification methods, and foaming property-imparting technologies (Patent Literatures 1 and 2). Furthermore, there have been reported methods for producing medium-chain sophorolipids mainly having a carbon chain length of 12, by applying genetic modification to *Starmerella bombicola* and thereby interrupting intracellular β-oxidation metabolism (Non Patent Literature 3, Patent Literature 3). In this genetic modification, MFE-2 (or FOX-2), which is a gene that is in charge of two reactions such as a hydroxylation reaction and a dehydrogenation reaction in β-oxidation of yeast in peroxisomes (Non Patent Literature 4), is deleted, and thereby a β-oxidation reaction is stopped.

Meanwhile, on the peroxisomes of yeast, PXA1 and PXA2 genes exist (Non Patent Literature 4). These two genes form a heterodimer, and the heterodimer works as a transporter transporting Acyl-CoA, which is a reaction substrate for β-oxidation. PXA1/PXA2 works as an ABC (ATP-binding cassette) transporter in an ATP-dependent manner, and mainly transports long-chained (>C16) Acyl-CoA into peroxisomes.

(Patent Literature 1) JP 2003-9896 A
(Patent Literature 2) JP 2014-150774 A
(Patent Literature 3) U.S. Pat. No. 8,530,206 B
(Non Patent Literature 1) Appl Microbiol Biotech, 2007, 76(1):23-34.
(Non Patent Literature 2) J SURFACT DETERG, 2006, 9, QTR 1:57-62
(Non Patent Literature 3) FEMS Yeast Res, 2009, 9:610-617
(Non Patent Literature 4) Cell Mol Life Sci, 2003, 60(9): 1838-1851

SUMMARY OF THE INVENTION

The present invention provides a sophorolipid-producing yeast mutant strain, in which a transporter transporting Acyl-CoA to a peroxisome has been deleted or deactivated.

The present invention also provides a method for producing a sophorolipid-producing yeast mutant strain, the method comprising deleting or deactivating a transporter transporting Acyl-CoA to a peroxisome in a sophorolipid-producing yeast.

Furthermore, the present invention provides a method for increasing the sophorolipid production capability of a sophorolipid-producing yeast, the method comprising deleting or deactivating a transporter transporting Acyl-CoA to a peroxisome in a sophorolipid-producing yeast.

Furthermore, the present invention provides a method for producing a sophorolipid, the method comprising culturing the sophorolipid-producing yeast mutant strain.

BRIEF DESCRIPTION OF THE DRAWINGS

FIG. 1 illustrates an increase in the sophorolipid production capability in a PXA1 gene- or PXA2 gene-deleted *Starmerella bombicola* mutant strain. Δpxa1: Δpxa1 mutant strain, Δpxa2: Δpxa2 mutant strain, PE: ethyl palmitate, SL: sophorolipid. Error bar=standard deviation (n=3).

FIG. 2 illustrates the amounts of various sophorolipids produced in *Starmerella bombicola* mutant strains. Δfox2: Δfox2 mutant strain, Δpxa1:Δpxa1 mutant strain. The term "C12 to C18" represents sophorolipids having constituent fatty acid chain lengths of C12 to C18, respectively. Error bar=standard deviation (n=3).

DETAILED DESCRIPTION OF THE INVENTION

The present invention relates to a yeast mutant strain capable of producing sophorolipids with high efficiency, and a method for producing a sophorolipid using the yeast mutant strain.

1. Definition

According to the present specification, the identity of nucleotide sequences and amino acid sequences is calculated according to the Lipman-Pearson method (Science, 1985, 227:1435-1441). Specifically, the identity is calculated by performing an analysis using the homology analysis program (Search Homology) of genetic information processing software, Genetyx-Win (Ver. 5.1.1; Software Development), with the unit size to compare (ktup) being set to 2.

According to the present specification, the phrase "at least 80% identity" in connection with nucleotide sequences and amino acid sequences means identity of 80% or higher, preferably 85% or higher, more preferably 90% or higher, evenmore preferably 95% or higher, even more preferably 98% or higher, even more preferably 99% or higher.

According to the present specification, "sophorolipid-producing yeast" refers to a yeast having an capability to produce sophorolipids. Examples of the sophorolipid-producing yeast include Ascomycetes such as the genus *Starmerella*, the genus *Candida*, and the genus *Wickerhamiella*, and preferred examples include *Starmerella bombicola*, *Candida bogoriensis*, *Candida batistae*, *Candida apicola*, and *Wickerhamiella domericqiae*. A more preferred example may be *Starmerella bombicola*.

2. Sophorolipid-Producing Yeast Mutant Strain

The inventors of the present invention found that a sophorolipid-producing yeast in which a transporter transporting Acyl-CoA to a peroxisome has been deleted or deactivated, increases the sophorolipid production capability of the yeast.

The present inventionprovides a yeast mutant strainhaving high sophorolipid production capability. According to the yeast mutant strain of the present invention, sophorolipids having constituent fatty acids with various chain lengths can be produced efficiently.

The sophorolipid-producing yeast mutant strain of the present invention is a mutant strain in which a transporter transporting Acyl-CoA to a peroxisome has been deleted or deactivated. Preferably, the sophorolipid-producing yeast mutant strain of the present invention is a mutant strainproduced by deleting or deactivating a transporter transporting Acyl-CoA to a peroxisome in a sophorolipid-producing yeast through artificial modification.

Preferably, the yeast mutant strain of the present invention, in which a transporter transporting Acyl-CoA to a peroxisome has been deleted or deactivated, is a mutant strain in which the activity of the transporter (that is, activity of transporting Acyl-CoA to a peroxisome) has been reduced or lost, as compared to the strain before mutation (parent strain). For example, in the mutant strain of the present invention, expression of the transporter is suppressed, or the transporter activity of the expressed protein has been reduced or lost.

Examples of the transporter transporting Acyl-CoA to a peroxisome in a sophorolipid-producing yeast include PXA1, PXA2, and proteins equivalent to those. Therefore, according to an embodiment, the mutant strain of the present invention may be a mutant strain in which the amount of any one of the transporter proteins expressed has been decreased to be 50% or less, preferably 40% or less, more preferably 30% or less, even more preferably 20% or less, even more preferably 10% or less, even more preferably 5% or less, as compared to the parent strain. The amount of a protein expressed can be measured by a conventionally used method for quantitatively determining the expression of a protein, for example, bymeasurement of the amount of mRNA through quantitative PCR, a colorimetric determination method, a fluorescence method, Western blotting, ELISA, or radioimmunoassay, without being limited to these.

According to the present specification, PXA1 is a protein consisting of the amino acid sequence set forth in SEQ ID NO:2. According to the present specification, PXA2 is a protein consisting of the amino acid sequence set forth in SEQ ID NO:4.

According to the present specification, a protein equivalent to PXA1 refers to a protein that consists of an amino acid sequence having at least 80% identity with the amino acid sequence set forth in SEQ ID NO: 2, and forms a heterodimer together with PXA2 or a protein equivalent thereto to thereby work as a transporter transporting Acyl-CoA to a peroxisome.

According to the present specification, a protein equivalent to PXA2 refers to a protein that consists of an amino acid sequence having at least 80% identity with the amino acid sequence set forth in SEQ ID NO: 4, and forms a heterodimer together with PXA1 or a protein equivalent thereto to thereby work as a transporter transporting Acyl-CoA to a peroxisome.

Examples of means for deletion or deactivation of the transporter include a method of deleting or deactivating a gene encoding the transporter. This method brings reduction or loss of the activity of transporting Acyl-CoA to a peroxisome in yeast by suppressing the amount of the expressed transporter protein, or by changing the activity of the expressed protein.

Therefore, according to an embodiment, the sophorolipid-producing yeast mutant strain of the present invention is a mutant strain in which a gene encoding a transporter that transports Acyl-CoA to a peroxisome has been deleted or deactivated. According to a preferred embodiment, the sophorolipid-producing yeast mutant strain of the present invention is a mutant strain in which PXA1 gene, PXA2 gene, or a gene equivalent thereto has been deleted or deactivated.

According to the present specification, PXA1 gene is a gene that encodes PXA1 protein consisting of the amino acid sequence set forth in SEQ ID NO: 2. PXA1 gene may be the nucleotide sequence set forth in SEQ ID NO: 1, a complementary strand thereof, or a gene consisting of DNA composed of those. Furthermore, according to the present specification, PXA2 gene is a gene that encodes PXA2 protein consisting of the amino acid sequence set forth in SEQ ID NO:4. PXA2 gene may be the nucleotide sequence set forth in SEQ ID NO:3, a complementary strand thereof, or a gene consisting of DNA composed of those.

A gene equivalent to PXA1 gene is a gene encoding a protein that forms a heterodimer together with PXA2 or a protein equivalent thereto to thereby work as a transporter transporting Acyl-CoA to a peroxisome. The gene equivalent to PXA1 gene may be a nucleotide sequence having at least 80% identity with the nucleotide sequence set forth in SEQ ID NO:1, a complementary strand thereof, or a gene consisting of DNA composed of those.

A gene equivalent to PXA2 gene is a gene encoding a protein that forms a heterodimer together with PXA1 or a protein equivalent thereof to thereby work as a transporter transporting Acyl-CoA to a peroxisome. The gene equivalent to PXA2 gene may be a nucleotide sequence having at least 80% identity with the nucleotide sequence set forth in SEQ ID NO:3, a complementary strand thereof, or a gene consisting of DNA composed of those.

Examples of means for deleting or deactivating a gene of a yeast cell include introduction of mutation (deletion, insertion, substitution, or addition) to one or more nucleotides on the nucleotide sequence of the target gene, substitution or insertion of another nucleotide sequence into the nucleotide sequence, or deletion of a portion or the entirety of the nucleotide sequence. Alternatively, similar introduction of mutation, or similar substitution, insertion or deletion of a nucleotide sequence may also be carried out with regard to the promoter region of the target gene.

Regarding a specific technique for the introduction of mutation or the substitution, insertion or deletion of a nucleotide sequence, a method for genetic modification of a microorganism that is known in the pertinent art can be used. Examples of the method include, but are not limited to, ultraviolet irradiation, introduction of a site-specific mutation, and homologous recombination method using the SOE-PCR method (splicing by overlap extension PCR; Gene, 1989, 77:61-68).

After the introduction of mutation, or the substitution, insertion or deletion of a nucleotide sequence, a genetic analysis is carried out, or the amount of an expressed protein encoded by the target gene or the activity thereof is evaluated, and cells having a desired mutation are selected, to thereby obtain the mutant strain of the present invention.

Alternatively, in a case where the means for deleting or deactivating a gene is the homologous recombination method using SOE-PCR, a mutant strain having the target gene deleted therefrom can be obtained by incorporating a drug resistance marker gene into a DNA fragment for gene deletion that substitutes the target gene DNA, culturing, on a medium including a drug, cells into which the DNA fragment for deletion has been introduced, and isolating growing colonies. Furthermore, mutation may also be checked by carrying out the genetic analysis or evaluating the amount of the protein expressed or activity of the protein as described above. By following the procedure described above, the yeast mutant strain of the present invention in which a gene that encodes a transporter transporting Acyl-CoA to a peroxisome has been deleted or deactivated can be obtained.

3. Increase of Sophorolipid Production Capability in Mutant Strain

The sophorolipid-producing yeast mutant strain of the present invention that has been produced by deletion or deactivation of a transporter transporting Acyl-CoA to a peroxisome as described above, has increased sophorolipid production capability, as compared to the strain before mutation (parent strain). Therefore, an embodiment of the present invention can be a method for increasing the sophorolipid production capability of a sophorolipid-producing yeast, the method comprising deleting or deactivating a transporter transporting Acyl-CoA to a peroxisome in a sophorolipid-producing yeast.

4. Production of Sophorolipids

The sophorolipid-producing yeast mutant strain of the present invention has increased sophorolipid production capability. Furthermore, the sophorolipid-producing yeast mutant strain of the present invention can produce sophorolipids using, for example, hydrocarbon chains and fatty acids having various chain lengths as substrates. Therefore, when the sophorolipid-producing yeast mutant strain of the present invention is cultured together with a substrate having an appropriate chain length, theyeastmutant strain can efficiently produce a sophorolipid including a constituent fatty acid having a desired chain length. Therefore, the present invention also provides a method for producing a sophorolipid, the method comprising culturing the sophorolipid-producing yeast mutant strain of the present invention.

In the method for producing a sophorolipid of the present invention, the mutant strain of the present invention is cultured in a medium including substrates such as a fatty acid, a fatty acid alkyl ester, an alkane, an alkene, an alkyne, an alcohol, a triacylglycerol, a diacylglycerol, a monoacylglycerol, and a fat or oil. Sophorolipids are collected from the medium after culturing and are appropriately purified as necessary, and thereby sophorolipids can be produced.

Regarding the medium used for the culture, any conventional medium containing a carbon source, a nitrogen source, an inorganic salt, and if necessary, organic trace nutrients such as amino acids and vitamins, can be used. The medium may be any of a synthetic medium and a natural medium.

The carbon source and the nitrogen source included in the medium may be any type of material that can be utilized by the mutant strain to be cultured. Examples of the carbon source include saccharides such as glucose, glycerol, fructose, sucrose, maltose, mannose, galactose, starch hydrolysate, and malt; organic acids such as acetic acid and citric acid; and alcohols such as ethanol. These carbon sources can be used singly or in combination of two or more kinds thereof. Examples of the nitrogen source include ammonia; ammonium salts such as ammonium sulfate, ammonium carbonate, ammonium chloride, ammonium phosphate, and ammonium acetate; and nitrates.

Examples of the inorganic salt include phosphates, magnesium salts, calcium salts, iron salts, and manganese salts. Examples of the organic trace nutrients include amino acids, vitamins, fatty acids, nucleic acids, and peptones, casamino acids, yeast extracts and soybean protein degradation products that contain the amino acids, vitamins, fatty acids and nucleic acids. Ina case where an auxotrophic mutant strain that requires, for example, amino acids for growth is used, it is preferable that the required nutrients are added as supplements.

Preferred examples of the substrate that can be incorporated into the medium include C12-20 fatty acids and alkyl esters thereof, C12-20 alkanes, C12-20 alkenes, C12-20 alkynes, C12-20 alcohols; triacylglycerols, diacylglycerols and monoacylglycerols, each containing C12-20 fatty acids or alkyl esters thereof; and fats or oils containing C12-20 fatty acids or alkyl esters thereof. More preferred examples include C12-18 fatty acids and alkyl esters thereof, C12-18 alkanes, C12-18 alkenes, C12-18 alkynes, C12-18 alcohols; triacylglycerols, diacylglycerols and monoacylglycerols, each containing C12-C18 fatty acids or alkyl esters thereof; and fats or oils containing C12-C18 fatty acids or alkyl esters thereof. Even more preferred examples include C12-C18 fatty acids and alkyl esters thereof.

More specific examples of the substrate, which are not limited, include, as the C12-20 fatty acids, dodecanoic acid (lauric acid), tridecanoic acid, tetradecanoic acid (myristic acid), pentadecaonic acid (pentadecyl acid), hexadecanoic acid (palmitic acid), hexadecenoic acid, heptadecanoic acid (margaric acid), octadecanoic acid (stearic acid), octadecenoic acid, octadecadienoic acid, octadecatrienoic acid, nonadecanoic acid, eicosanoic acid, eicosadienoic acid, eicosatrienoic acid, and eicosatetraenoic acid; as the C12-20 alkanes, alkenes, alkynes and alcohols, dodecane, tridecane, tetradecane, pentadecane, hexadecane, hexadecene, heptadecane, octadecane, octadecene, octadecyne, nonadecane, eicosane, eicosene, eicosyne, dodecanol, tridecanol, tetradecanol, pentadecanol, hexadecanol, hexadecenal, heptadecanol, octadecanol, octadecenol, octadecynol, nonadecanol, and eicosanol; and as the fats or oils containing C12-20 fatty acids or alkyl esters thereof, coconut oil, palm oil, palm kernel oil, olive oil, rapeseed oil, rice bran oil, soybean oil, castor oil, and mahua oil.

Examples of the fatty acid alkyl esters include alkyl esters of the fatty acids mentioned above wherein the alkyl moiety has 1 to 4 carbon atoms, and preferred examples include methyl esters and ethyl esters.

The substrates mentioned above can be used singly or in combination of two or more kinds thereof. Preferably, a fatty acid having any chain length between C12 and C18; an alkyl ester thereof; a triacylglycerol, a diacylglycerol, a monoacylglycerol, or fats or oils, each containing the fatty acid or an alkyl ester thereof, or an alkane, an alkene, an alkyne, or an alcohol, each having any chain length between C12 and 18, is used. More preferably, a fatty acid having any chain length between C12 and C18, or an alkyl ester thereof is used.

The content of the substrate (at the time of initiation of culturing) that can be included in the medium is preferably 1% by mass or more, more preferably 3% by mass or more, even more preferably 5% by mass or more, and is preferably 30% by mass or less, more preferably 20% by mass or less, even more preferably 15% by mass or less. Alternatively, the content is preferably from 1% to 30% by mass, from 1% to 20% by mass, from 1% to 15% by mass, from 3% to 30% by mass, from 3% to 20% by mass, from 3% to 15% by mass, from 5% to 30% by mass, from 5% to 20% by mass, or from 5% to 15% by mass.

The culture conditions may be any conditions in which sophorolipids are fermentatively produced by the mutant strain of the present invention. Culturing is preferably carried out under aerobic conditions, and general methods such as aerated and agitated culture and shaking culture can be applied. The culturing temperature is preferably from 20° C. to 33° C., more preferably from 25° C. to 30° C., even more preferably from 28° C. to 30° C. The initial pH (30° C.) of the medium is preferably from 2 to 7, more preferably from 3 to 6. The culturing time is preferably about from 24 hours to 200 hours, more preferably from 50 to 200 hours.

In regard to the culturing described above, sophorolipids may be produced fermentatively by culturing the mutant strain of the present invention under the conditions that enables proliferation of cells, and sophorolipids may also be produced fermentatively by culturing the mutant strain of the present invention in the state of a resting cell, that is, in a state in which growth and proliferation has been stopped.

The method of collecting sophorolipids from the medium after culturing is not particularly limited, and collection may be performed according to any known collecting method. For example, the sophorolipids in the medium can be collected or purified by performing, for example, solvent extraction using, for example, ethyl acetate, fractional precipitation, liquid-liquid partition, column chromatography, high performance liquid chromatography, singly or in appropriate combination.

5. Exemplary Embodiments

As exemplary embodiments of the present invention, for example, the following substances, production methods, use, and methods will be further disclosed in the present specification. However, the present invention is not intended to be limited to these embodiments.

[1] A sophorolipid-producing yeast mutant strain, in which a transporter transporting Acyl-CoA to a peroxisome has been deleted or deactivated.

[2] The mutant strain according to [1], wherein the transporter transporting Acyl-CoA to a peroxisome is preferably PXA1, PXA2, or a protein equivalent thereto.

[3] The mutant strain according to [2], wherein preferably, the PXA1 is a protein consisting of the amino acid sequence set forth in SEQ ID NO:2, the PXA2 is a protein consisting of the amino acid sequence set forth in SEQ ID NO:4, the protein equivalent to PXA1 is a protein consisting of an amino acid sequence having at least 80% identity with the amino acid sequence set forth in SEQ ID NO:2, and forming a heterodimer together with PXA2 or a protein equivalent thereto to work as a transporter transporting Acyl-CoA to a peroxisome, and the protein equivalent to PXA2 is a protein consisting of an amino acid sequence having at least 80% identity with the amino acid sequence set forth in SEQ ID NO:4, and forming a heterodimer together with PXA1 or a protein equivalent thereto to work as a transporter transporting Acyl-CoA to a peroxisome.

[4] The mutant strain according to [2] or [3], wherein preferably, PXA1 gene, PXA2 gene, or a gene equivalent thereto has been deleted or deactivated.

[5] The mutant strain according to [4], wherein preferably, the PXA1 gene is a gene encoding a protein consisting of the amino acid sequence set forth in SEQ ID NO:2, the PXA2 gene is a gene encoding a protein consisting of the amino acid sequence set forth in SEQ ID NO:4, the gene equivalent to PXA1 gene is a gene encoding a protein that forms a heterodimer together with PXA2 or a protein equivalent thereto to thereby work as a transporter transporting Acyl-CoA to a peroxisome, and the gene equivalent to PXA2 gene is a gene encoding a protein that forms a heterodimer together with PXA1 or a protein equivalent thereto to thereby work as a transporter transporting Acyl-CoA to a peroxisome.

[6] The mutant strain according to any one of [1] to [5], wherein the sophorolipid-producing yeast is preferably a microorganism of the genus *Starmerella*, more preferably *Starmerella bombicola*.

[7] The mutant strain according to any one of [1] to [6], wherein the mutant strain has increased sophorolipid productivity, as compared to the strain before mutation.

[8] A method for producing a sophorolipid-producing yeast mutant strain, the method comprising deleting or deactivating a transporter transporting Acyl-CoA to a peroxisome in a sophorolipid-producing yeast.

[9] A method for increasing the sophorolipid production capability of a sophorolipid-producing yeast, the method comprising deleting or deactivating a transporter transporting Acyl-CoA to a peroxisome in a sophorolipid-producing yeast.

[10] The method according to [8] to [9], wherein the transporter transporting Acyl-CoA to a peroxisome is preferably PXA1, PXA2, or a protein equivalent thereto.

[11] The method according to [10], wherein preferably, the PXA1 is a protein consisting of the amino acid sequence set forth in SEQ ID NO:2, the PXA2 is a protein consisting of the amino acid sequence set forth in SEQ ID NO:4, the protein equivalent to PXA1 is a protein consisting of an amino acid sequence having at least 80% identity with the amino acid sequence set forth in SEQ ID NO:2, and forming a heterodimer together with PXA2 or a protein equivalent thereto to work as a transporter transporting Acyl-CoA to a peroxisome, and the protein equivalent to PXA2 is a protein consisting of an amino acid sequence having at least 80% identity with the amino acid sequence set forth in SEQ ID NO:4and forming a heterodimer together with PXA1 or a protein equivalent thereto to work as a transporter transporting Acyl-CoA to a peroxisome.

[12] The method according to [10] or [11], preferably comprising deleting or deactivating PXA1 gene, PXA2 gene, or a gene equivalent thereto.

[13] The method according to [12], wherein preferably, the PXA1 gene is a gene encoding a protein consisting of the amino acid sequence set forth in SEQ ID NO:2,
the PXA2 gene is a gene encoding a protein consisting of the amino acid sequence set forth in SEQ ID NO:4,
the gene equivalent to PXA1 gene is a gene encoding a protein that forms a heterodimer together with PXA2 or a protein equivalent thereto, to thereby work as a transporter transporting Acyl-CoA to a peroxisome, and
the gene equivalent to PXA2 gene is a gene encoding a protein that forms a heterodimer together with PXA1 or a protein equivalent thereto, to thereby work as a transporter transporting Acyl-CoA to a peroxisome.

[14] The method according to any one of [8] to [13], wherein the sophorolipid-producing yeast is preferably a microorganism of the genus *Starmerella*, more preferably *Starmerella bombicola*.

[15] A method for producing a sophoroliplid, the method comprising culturing the sophorolipid-producing yeast mutant strain according to any one of [1] to [7].

[16] The method according to [15], wherein a medium for the culturing preferably comprises the following substrate:
at least one substrate selected from the group consisting of C12-C20 fatty acids and alkyl esters thereof, C12-C20 alkanes, C12-C20 alkenes, C12-C20 alkynes, C12-C20 alcohols, triacylglycerols, diacylglycerols and monoacylglycerols each of which comprises C12-C20 fatty acids or alkyl esters thereof, and fats or oils comprising C12-C20 fatty acids or alkyl esters thereof;
at least one substrate selected from the group consisting of C12-C18 fatty acids and alkyl esters thereof, C12-C18 alkanes, C12-C18 alkenes, C12-C18 alkynes, C12-C18 alcohols, triacylglycerols, diacylglycerols and monoacylglycerols each of which comprises C12-C18 fatty acids or alkyl esters thereof, and fats or oils comprising C12-C18 fatty acids or alkyl esters thereof; or
at least one substrate selected from the group consisting of C12-18 fatty acids and alkyl esters thereof.

[17] The method according to [16], wherein the content of the substrate in the medium is:
preferably 1% by mass or more, more preferably 3% by mass or more, even more preferably 5% by mass or more, and is preferably 30% by mass or less, more preferably 20% by mass or less, even more preferably 15% by mass or less, or
preferably from 1% to 30% by mass, from 1% to 20% by mass, from 1% to 15% by mass, from 3% to 30% by mass, from 3% to 20% by mass, from 3% to 15% by mass, from 5% to 30% by mass, from 5% to 20% by mass, or from 5% to 15% by mass.

[18] The method according to any one of [15] to [17], wherein the method further comprises collecting sophorolipids from the medium after the culturing.

EXAMPLES

Hereinafter, the present invention will be more specifically described by way of Examples.

Example 1

Production of Gene-Deleted Mutant Strain (1) Establishment of Fragment for Gene Deletion Mutant strains having PXA1 gene, PXA2 gene, or FOX2 gene deleted therefrom were produced by a homologous recombination method using the SOE-PCR method.

A hygromycin-resistant gene (SEQ ID NO:5) was used for the selection of transformant. A hygromycin-resistant gene fragment was produced by PCR using plasmid loxP-PGK-gb2-hygro-loxP (Gene Bridges) having a hygromycin-resistant gene as a template, and using primers of SEQ ID NO:18 and SEQ ID NO:19. Fragments of a promoter and a terminator of URA3 gene were produced by PCR using the genome of *Starmerella bombicola* as a template, and using primers of SEQ ID NO:20 and SEQ ID NO:21, and primers of SEQ ID NO:22 and SEQ ID NO:23, respectively. The hygromycin-resistant gene fragment was ligated to the promoter fragment and the terminator fragment of URA3 gene by SOE-PCR.

A fragment for deleting PXA1 gene, PXA2 gene or FOX2 gene was produced. Using the genome of *Starmerella bombicola* as a template, fragments in the upstream region of each gene were produced by PCR using primers of SEQ ID NO:6 and SEQ ID NO:7, primers of SEQ ID NO:8 and SEQ ID NO:9, and primers of SEQ ID NO:10 and SEQ ID NO:11, respectively, while fragments in the downstream region of each gene were produced by PCR using primers of SEQ ID NO:12 and SEQ ID NO:13, primers of SEQ ID NO:14 and SEQ ID NO:15, and primers of SEQ ID NO:16 and SEQ ID NO:17, respectively. Furthermore, a hygromycin-resistant gene fragment including the promoter fragment and the terminator was produced by PCR using the SOE-PCR product as a template, and using primers of SEQ ID NO:20 and SEQ ID NO:23. Three fragments, namely, the thus-obtained upstream region fragment and the downstream region fragment of each gene and the hygromycin-resistant gene fragment, were ligated by SOE-PCR. The fragments thus obtained were respectively used as fragments for deletion of PXA1 gene, PXA2 gene, and FOX2 gene.

TABLE 1

| SEQ ID NO. | Primer name | Sequence (5'→3') |
|---|---|---|
| 6 | pxa1upFw | ATTTTGGAGAGTTTGTGACTGCTTTATCAA |
| 7 | pxa1upRv | GTTGCGAGCTGTTTCGAAAATTACACTATCATCCGGAGCGTGTGGGGTCA |
| 8 | pxa2upFw | GGCATCAATTAATCACAACTAGCTTTCTCG |
| 9 | pxa2upRv | GTTGCGAGCTGTTTCGAAAATTGAACTAAAGTTCTCCGTGCAGATATTTG |
| 10 | fox2upFw | CTGAATTCTCCTAAGCATTTAACTGCCTTG |
| 11 | fox2upRv | GTTGCGAGCTGTTTCGAAAAGTTTCACTTTCCCTTCTTGTATTTTCAATG |
| 12 | pxa1doFw | tgtatagtgacgatgatgaaTTTGGCTACAACTACCATCAGGGTCGTTAG |
| 13 | pxa1doRv | TGAGATGACACACGTGACATGTCGATCCTA |
| 14 | pxa2 doFw | tgtatagtgacgatgatgaaCGATCTTGCGAACGCTAAAACCAGTAGTTT |
| 15 | pxa2 doRv | TAGCGCAGAGCAGTATGCCCCCTTCTTCCC |

TABLE 1-continued

| SEQ ID NO. | Primer name | Sequence (5'→3') |
|---|---|---|
| 16 | fox2 doFw | tgtatagtgacgatgatgaaCGGAGAAGCTATATAGTTAAATAAATAAGA |
| 17 | fox2 doRv | ATGCATAATGTGCGCTTCCGCTCTGAGACA |
| 18 | Hyg-fw | CACTACTGTAGAGAAATAATATGAAAAAGCCTGAACTCAC |
| 19 | Hyg-re | GAAGGAACTGTTTGAGAAAATTATGAACAAACGACCCAAC |
| 20 | pURA3-fw | TTTTCGAAACAGCTCGCAACGATC |
| 21 | pUra3-re | GTGAGTTCAGGCTTTTTCATATTATTTCTCTACAGTAGTG |
| 22 | tURA3-fw | GTTGGGTCGTTTGTTCATAATTTTCTCAAACAGTTCCTTC |
| 23 | tURA3-re | TTCATCATCGTCACTATACACATC |

(2) Production of Gene Deletion Strain

One platinum loop of *Starmerella bombicola* was inoculated into a 100-mL type test tube containing 5 mL of YPD Broth, and the cells were cultured for 48 hours at 30° C. and 250 rpm. The culture fluid thus obtained was inoculated in an amount of 1% (v/v) into a Sakaguchi flask containing 50 mL of YPD medium, and the cells were cultured at 30° C. and 120 rpm until an OD600 value of 1 to 2 was obtained. The proliferated cells were centrifuged for 5 minutes at 3,000 rpm and 4° C. to collect the cells, and then the cells were washed twice with 20 mL of sterilized water that had been chilled on ice. The cells were suspended in 1 mL of an ice-cooled 1 M sorbitol solution, and the suspension was centrifuged for 5 minutes at 5,000 rpm and 4° C. The supernatant was discarded, subsequently 400 µL of a 1 M sorbitol solution was added to the residue, the mixture was placed on ice, and the mixture was suspended by pipetting. This yeast suspension was dispensed into 50 µL each, and 1 µg of a DNA solution for transformation (including the fragment for deletion of PXA1 gene, PXA2 gene, or FOX2 gene) was added to the yeast suspension. The mixture was transferred into an ice-cooled chamber having a 0.2 cm gap. Subsequently, a pulse of 25 µF, 350Ω, and 2.5 kV was applied to the mixture using a GENE PULSER II (Bio-Rad). An ice-cooled 1 M sorbitol-containing YPD Broth was added to the mixture to which a pulse had been applied, the mixture was transferred into a tube having a capacity of 1.5 mL, and the mixture was shaken for 2 hours at 30° C. Subsequently, the mixture was centrifuged for 5 minutes at 5,000 rpm and 4° C., to thereby collect the cells. The cells thus collected were resuspended in 200 µL of a 1 M sorbitol solution, 100 µL each of the suspension was smeared on a selective medium, and the cells were cultured for about one week at 30° C. For the selective medium, an agar medium containing 1% (w/v) of anyeast extract, 2% (w/v) of peptone, 2% (w/v) of glucose, and 500 ppm of hygromycin was used. Colonies that had grown were subjected to colony PCR, it was confirmed that the sequence length amplified from the region of each deletion target gene was changed, and thus mutant strains having PXA1 gene, PXA2 gene, or FOX2 gene deleted therefrom (Δpxa1 mutant strain, Δpxa2 mutant strain, and Δfox2 mutant strain) were obtained.

Example 2

Sophorolipid Productivity of Δpxa1 Mutant Strain and Δpxa2 Mutant Strain (1) Culture of Mutant Strains 5 mL of a medium containing 1% (w/v) of a yeast extract that had been sterilized in advance, 2% (w/v) of peptone, and 2% (w/v) of glucose was introduced into a large-sized test tube, and one platinum loop of any one of the Δpxa1 mutant strain and Δpxa2 mutant strain obtained in Example 1 as well as the parent strain thereof was inoculated into the medium. The cells were subjected to shaking culture for 48 hours at 30° C. and 250 rpm, and this was used as a seed culture fluid. The seed culture fluid was inoculated at a concentration of 1% (v/v) into 5 mL of a mixed medium containing, 2% (w/v) of a yeast extract, 5% (w/v) of a fatty acid ester, and 12.5% (w/v) of glucose, and shaking culture was carried out for 96 hours at 30° C. and 250 rpm. Ethyl palmitate was used as the fatty acid ester.

(2) Evaluation of Sophorolipid Productivity

After completion of the culturing, ethyl palmitate (PE) and sophorolipids (SL) in the culture fluid were extracted, and the amounts thereof were measured. For the extraction of PE, first, the entire amount of the culture fluid in the large-sized test tube cultured in section (1) was transferred into a Falcon tube (Greiner), subsequently 4 mL of hexane was added to the large-sized test tube and stirred by vortexing for 5 seconds, and the entire amount was transferred to the same Falcon tube. The liquids were thoroughly mixed by vortexing for 5 seconds, and subsequently the liquid was centrifuged for 5 minutes at 3,000 rpm and 25° C. The entire amount of the hexane fraction of the supernatant was collected into a glass tube using a Pasteur pipette. Hexane extraction as described above was repeated once for the remaining liquid, and thereby the entire amount of PE was extracted. For the extraction of SL, 4 mL of ethyl acetate was added to the large-sized test tube that had been used for culturing in section (1), the mixture was vortexed for 5 seconds, and the entire amount was collected into a Falcon tube. Subsequently, the liquid was centrifuged for 5 minutes at 3,000 rpm and 25° C., and the entire amount of the ethyl acetate fraction of the supernatant was collected into a fresh glass tube using a Pasteur pipette. The above-described ethyl acetate extraction was repeated once for the remaining liquid, and thereby, the entire amount of SL was collected.

Hexane or ethyl acetate was volatilized from the hexane fraction or the ethyl acetate fraction thus collected, by spraying nitrogen gas, and thus dissolved PE or SL was extracted. The difference between the weight of the glass tube containing PE or SL thus extracted, and the weight of the glass tube before collection, was calculated as the amount of PE or the amount of SL in the culture fluid.

The result is presented in FIG. 1. The relative values of sophorolipid productivity of each mutant strain in the case of designating the sophorolipidproductivity of the parent strain as 100%, are presented in Table 2. The mutant strains with deleted PXA1 gene or PXA2 gene showed increased sophorolipid productivity, as compared to the parent strain.

TABLE 2

| | Relative amount of SL produced |
|---|---|
| Parent strain | 100% |
| Δpxa1 | 126% |
| Δpxa2 | 112% |

Example 3

Comparison of Sophorolipid Productivity between Δpxa1 Mutant Strain and Δfox2 Mutant Strain Δpxa1 mutant strain, Δfox2 mutant strain, and their parent strain were cultured by a procedure similar to that of Example 2, and the amounts of fatty acid ester and sophorolipids in the culture fluid were measured. However, the culturing time in the mixed medium containing a fatty acid ester was changed to 72 hours, and ethyl laurate (C12), ethyl myristate (C14), ethyl palmitate (C16), or ethyl stearate (C18) was used as the fatty acid ester.

The result is presented in FIG. 2. Furthermore, the relative values of sophorolipid productivity of Δfox2 mutant strain and Δpxa1 mutant strain obtained in a case in which the sophorolipid productivity of the parent strain obtained by using the fatty acids having each chain length as substrates, was designated as 100%, are presented in Table 3.

It has been reported that the productivity for medium-chain sophorolipids is increased by destruction of FOX2 gene, which is related to the β-oxidation metabolism of yeast (Non Patent Literature 3 and Patent Literature 3). In this Example as well, the Δfox2 mutant strain exhibited increased sophorolipid productivity, as compared to the parent strain, when C12 and C14 fatty acids were used as substrates. However, when C16 and C18 fatty acids were used as substrates, the sophorolipid productivity was decreased, as compared to that of the parent strain. On the other hand, the Δpxa1 mutant strain of the present invention showed even higher sophorolipid productivity than that of the Δfox2 mutant strain when C12 and C14 fatty acids were used as substrates. Furthermore, the Δpxa1 mutant strain showed increased sophorolipid productivity, as compared to the parent strain, even in the case of using any of C12, C14, C16, and C18 fatty acids as the substrate.

TABLE 3

| | Substrate carbon chain length | | | |
|---|---|---|---|---|
| | C12 | C14 | C16 | C18 |
| Parent strain | 100% | 100% | 100% | 100% |
| Δfox2 strain | 268% | 123% | 32% | 36% |
| Δpxa1 strain | 360% | 188% | 112% | 112% |

What is claimed is:

1. A sophorolipid-producing yeast mutant strain, in which a transporter that transports Acyl-CoA to a peroxisome has been deleted or deactivated, and in which the sophorolipid production capability is increased as compared to the sophorolipid production capability of its parent strain in which the transporter is not deleted or deactivated, wherein the transporter that is deleted or deactivated comprises at least one protein selected from the group consisting of:
(a) a PXA1 protein having the amino acid sequence of SEQ ID NO:2,
(b) a PXA2 protein having the amino acid sequence of SEQ ID NO:4,
(c) a protein having an amino acid sequence that has at least 90% amino acid sequence identity with the amino acid sequence of SEQ ID NO:2 and that forms a heterodimer with the PXA2 protein of part (b), the heterodimer having the activity of transporting Acyl-CoA to a peroxisome, and
(d) a protein having an amino acid sequence that has at least 90% amino acid sequence identity with the amino acid sequence of SEQ ID NO:4 and that forms a heterodimer with the PXA1 protein of part (a), the heterodimer having the activity of transporting Acyl-CoA to a peroxisome.

2. The mutant strain according to claim 1, wherein the transporter that is deleted or deactivated is
(a) the PXA1 protein having the amino acid sequence of SEQ ID NO:2,
(b) the PXA2 protein having the amino acid sequence of SEQ ID NO:4, or both (a) and (b).

3. The mutant strain according to claim 1, wherein the % sequence identity of the protein of parts (c) and (d) is 95%.

4. The mutant strain according to claim 1, wherein the gene encoding the protein of part (a), (b), (c) or (d) has been deleted or deactivated.

5. The mutant strain according to claim 4, wherein the gene encoding the protein of part (a) or (b), or both, has been deleted or deactivated.

6. The mutant strain according to claim 1, wherein the sophorolipid-producing yeast is a microorganism of the genus *Starmerella*.

7. A method for producing a sophorolipid-producing yeast mutant strain, the method comprising deleting or deactivating a transporter that transports Acyl-CoA to a peroxisome in a sophorolipid-producing yeast wherein the sophorolipid production capability is increased in the mutant strain as compared to that of its parent strain in which that transporter is not deleted or deactivated, wherein the transporter that is deleted or deactivated comprises at least one protein selected from the group consisting of:
(a) a PXA1 protein having the amino acid sequence of SEQ ID NO:2,
(b) a PXA2 protein having the amino acid sequence of SEQ ID NO:4,
(c) a protein having an amino acid sequence that has at least 90% amino acid sequence identity with the amino acid sequence of SEQ ID NO:2 and that forms a heterodimer with the PXA2 protein of part (b), the heterodimer having the activity of transporting Acyl-CoA to a peroxisome, and
(d) a protein having an amino acid sequence that has at least 90% amino acid sequence identity with the amino acid sequence of SEQ ID NO:4 and that forms a heterodimer with the PXA1 protein of part (a), the heterodimer having the activity of transporting Acyl-CoA to a peroxisome.

8. The method according to claim 7, wherein the transporter that is deleted or deactivated is
(a) the PXA1 protein having the amino acid sequence of SEQ ID NO:2,
(b) the PXA2 protein having the amino acid sequence of SEQ ID NO:4, or both (a) and (b).

9. The method according to claim 7, wherein the % sequence identity of the protein of parts (c) and (d) is 95%.

10. The method according to claim 7, comprising deleting or deactivating the gene encoding the protein of part (a), (b), (c) or (d).

11. The method according to claim 10, wherein the gene encoding the protein of part (a) or (b), or both, has been deleted or deactivated.

12. The method according to claim 7, wherein the sophorolipid-producing yeast is a microorganism of the genus *Starmerella*.

13. The method according to claim 12, wherein the *Starmerella* is *Starmerella bombicola*.

14. The method according to claim 8, wherein the transporter that is deleted or deactivated is
(a) the PXA1 protein having the amino acid sequence of SEQ ID NO:2.

15. The method according to claim 8, wherein the transporter that is deleted or deactivated is (b) the PXA2 protein having the amino acid sequence of SEQ ID NO:4.

16. The method according to claim 8, wherein the transporter that is deleted or deactivated is both
   (a) the PXA1 protein having the amino acid sequence of SEQ ID NO:2, and
   (b) the PXA2 protein having the amino acid sequence of SEQ ID NO:4.

17. A method for producing a sophorolipid, the method comprising culturing the sophorolipid-producing yeast mutant strain according to claim 1.

18. The method according to claim 17, wherein the culturing is in a medium that comprises at least one substrate selected from the group consisting of C12-C20 fatty acids and alkyl esters thereof, C12-C20 alkanes, C12-C20 alkenes, C12-C20 alkynes, C12-C20 alcohols, and triacylglycerols, diacylglycerols, monoacylglycerols, and fats or oils, each comprising C12-C20 fatty acids or alkyl esters thereof.

19. The method according to claim 18, wherein the medium contains from 1% to 30% by mass of the substrate at the time of initiation of the culturing.

20. The method of claim 17, wherein the transporter that is deleted or deactivated in the yeast mutant strain of claim 1 is
   (a) the PXA1 protein having the amino acid sequence of SEQ ID NO:2,
   (b) the PXA2 protein having the amino acid sequence of SEQ ID NO:4, or
   (c) both (a) and (b).

21. The method of claim 20, wherein the gene encoding the protein of part (a) or (b) has been deleted or deactivated, or, the genes encoding both (a) and (b) have been deleted or deactivated.

* * * * *